(12) United States Patent
Liang et al.

(10) Patent No.: US 8,962,252 B2
(45) Date of Patent: Feb. 24, 2015

(54) OPTICAL SYSTEM FOR HIGH RESOLUTION THERMAL MELT DETECTION

(75) Inventors: Hongye Liang, Clarksville, MD (US); Kenton C. Hasson, Germantown, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 96 days.

(21) Appl. No.: 13/222,487

(22) Filed: Aug. 31, 2011

(65) Prior Publication Data

US 2012/0052563 A1    Mar. 1, 2012

Related U.S. Application Data

(60) Provisional application No. 61/378,471, filed on Aug. 31, 2010.

(51) Int. Cl.
| | |
|---|---|
| *C12Q 1/68* | (2006.01) |
| *H04N 7/18* | (2006.01) |
| *B01L 3/00* | (2006.01) |
| *B01L 7/00* | (2006.01) |
| *G01N 21/64* | (2006.01) |

(52) U.S. Cl.
CPC ............... *C12Q 1/68* (2013.01); *H04N 7/183* (2013.01); *B01L 3/5027* (2013.01); *C12Q 1/686* (2013.01); *B01L 7/52* (2013.01); *G01N 21/6456* (2013.01); *B01L 3/502715* (2013.01); *B01L 2300/0816* (2013.01); *B01L 2400/049* (2013.01)
USPC ........................................................ 435/6.12

(58) Field of Classification Search
CPC . G01N 21/6456; G01N 21/6458; C12Q 1/686
USPC ......................................................... 435/6.12
See application file for complete search history.

(56) References Cited

U.S. PATENT DOCUMENTS

| | | | |
|---|---|---|---|
| 5,852,495 | A | 12/1998 | Parce |
| 6,785,414 | B1 | 8/2004 | McStravick, III et al. |
| 6,960,437 | B2 | 11/2005 | Enzelberger et al. |
| 7,593,560 | B2 | 9/2009 | Hasson et al. |
| 7,629,124 | B2 | 12/2009 | Hasson et al. |

(Continued)

FOREIGN PATENT DOCUMENTS

| | | |
|---|---|---|
| WO | 2005/075683 A1 | 8/2005 |
| WO | 2009/051416 A1 | 4/2009 |

OTHER PUBLICATIONS

Kopp et al., "Chemical Amplification: Continuous-Flow PCR on a Chip," Science, 280(15), pp. 1046-1048 (1998).

(Continued)

*Primary Examiner* — Jonathan Hurst
(74) *Attorney, Agent, or Firm* — Rothwell, Figg, Ernst & Manbeck, P.C.

(57) ABSTRACT

This invention relates to systems and methods for imaging sample materials within a microfluidic device during an assay reaction process. In accordance with certain aspects of the invention, images are formed with a pixel array and a region of interest ("ROI") is defined within the pixel array. Image values, such as fluorescent intensity, can be computed as averages of individual pixel values within the ROI. Where the ROI is subject to non-uniform conditions, such as non-uniform heating, the ROI can be divided into sub-ROIs which are sufficiently small that the condition is uniform within the sub-ROI.

9 Claims, 3 Drawing Sheets

(56) References Cited

U.S. PATENT DOCUMENTS

| | | |
|---|---|---|
| 7,738,032 B2 | 6/2010 | Kollias et al. |
| 2005/0042639 A1 | 2/2005 | Knapp et al. |
| 2006/0094108 A1 | 5/2006 | Yoder et al. |
| 2006/0256228 A1* | 11/2006 | Konno ............................ 348/335 |
| 2008/0003588 A1 | 1/2008 | Hasson et al. |
| 2008/0003664 A1 | 1/2008 | Tysoe et al. |
| 2008/0056950 A1 | 3/2008 | Weisbuch et al. |
| 2008/0130971 A1* | 6/2008 | Hasson et al. ................ 382/129 |
| 2008/0176230 A1 | 7/2008 | Owen et al. |
| 2008/0199948 A1 | 8/2008 | Tafas et al. |
| 2008/0214412 A1 | 9/2008 | Stahler et al. |
| 2009/0248349 A1 | 10/2009 | Hasson et al. |
| 2009/0280485 A1* | 11/2009 | Flores Hernandez et al. .... 435/6 |
| 2009/0294703 A1 | 12/2009 | Unger et al. |
| 2009/0324037 A1 | 12/2009 | Hasson et al. |
| 2010/0015611 A1* | 1/2010 | Webster et al. .................. 435/6 |
| 2010/0021915 A1 | 1/2010 | Khan et al. |
| 2010/0075312 A1 | 3/2010 | Davies et al. |
| 2010/0103416 A1 | 4/2010 | Oldham et al. |
| 2010/0149392 A1 | 6/2010 | Hara |
| 2010/0285594 A1* | 11/2010 | Purvis, Jr. ....................... 436/10 |
| 2010/0330578 A1* | 12/2010 | Duhr et al. ........................ 435/6 |
| 2011/0048547 A1 | 3/2011 | Hasson et al. |

OTHER PUBLICATIONS

Lagally et al., "Single-Molecule DNA Amplification and Analysis in an Integrated Microfluidic Device," Analytical Chemistry, 73(3), pp. 565-570 (2001).

Park et al., "Cylindrical compact thermal-cycling device for continuous-flow polymerase chain reaction," Analytical Chemistry, 75, pp. 6029-6033 (2003).

PCT International Search Report and Written Opinion, issued in PCT/US11/50018 on Mar. 26, 2012, 18 pages.

* cited by examiner

OPTICAL SYSTEM FOR HIGH RESOLUTION THERMAL MELT DETECTION

CROSS-REFERENCE TO RELATED APPLICATION

This application claims the benefit of priority to U.S. Provisional Application No. 61/378,471, filed Aug. 31, 2010, the disclosure of which is hereby incorporated by reference in its entirety.

BACKGROUND

1. Field of the Invention

This invention relates to systems and methods for imaging sample materials within a microfluidic device during an assay reaction process.

2. Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase chain reaction (PCR) is a well-known technique for amplifying DNA.

With PCR, one can quickly produce millions of copies of DNA starting from a single template DNA molecule. PCR includes a three phase temperature cycle of denaturation of the DNA into single strands, annealing of primers to the denatured strands, and extension of the primers by a thermostable DNA polymerase enzyme. This cycle is repeated a number of times so that at the end of the process there are enough copies to be detected and analyzed. For general details concerning PCR, see Sambrook and Russell, Molecular Cloning—A Laboratory Manual (3rd Ed.), Vols. 1-3, Cold Spring Harbor Laboratory, Cold Spring Harbor, N.Y. (2000); Current Protocols in Molecular Biology, F. M. Ausubel et al., eds., Current Protocols, a joint venture between Greene Publishing Associates, Inc. and John Wiley & Sons, Inc., (supplemented through 2005) and PCR Protocols A Guide to Methods and Applications, M. A. Innis et al., eds., Academic Press Inc. San Diego, Calif. (1990).

In some applications, it is important to monitor the accumulation of DNA products as the amplification process progresses. Real-time PCR refers to a growing set of techniques in which one measures the buildup of amplified DNA products as the reaction progresses, typically once per PCR cycle. Monitoring the amplification process over time allows one to determine the efficiency of the process, as well as estimate the initial concentration of DNA template molecules. For general details concerning real-time PCR see Real-Time PCR: An Essential Guide, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (Anal Chem 73:565-570 (2001)), Kopp et al. (Science 280:1046-1048 (1998)), Park et al. (Anal Chem 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Further examples of systems, methods, and apparatus for high throughput approaches to performing PCR and other amplification reactions are described in the following publications that are related to the subject matter of the present disclosure.

U.S. Patent Application Publication No. 2008/0176230 to Owen et al. entitled "Systems and methods for real-time PCR" (the '230 publication"), the disclosure of which is hereby incorporated by reference, describes systems and methods for the real-time amplification and analysis of a sample of DNA within a micro-channel.

U.S. Pat. No. 7,629,124 to Hasson et al. entitled "Real-time PCR in micro-channels" (the '124 patent") the disclosure of which is hereby incorporated by reference, describes systems and methods for performing real time PCR in micro-channels by continuously moving boluses of test solution separated by carrier fluid through the micro-channels and performing a process, such as PCR, on each bolus and measuring signals, such as fluorescent signals, at different locations along a defined section of the channel.

U.S. Pat. No. 7,593,560 to Hasson et al. entitled "Systems and methods for monitoring the amplification and dissociation behavior of DNA molecules" (the '560 patent"), the disclosure of which is hereby incorporated by reference, describes the use of sensors for monitoring reactions within microfluidic channels. The sensor has a defined pixel array for collecting image data, and image data from a select window of pixels (a sub-set of the entire array), which encompasses a portion of interest of a micro-channel, is processed and stored for each of the micro-channels.

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA) with increasing temperature. The process of causing DNA to transition from dsDNA to ssDNA is sometimes referred to as a "high-resolution temperature (thermal) melt (HRTm)" process, or simply a "high-resolution melt" process.

To monitor a PCR process and/or a melting process (quantitatively and/or qualitatively), an imaging system may be employed to measure an optically detectable characteristic, such as fluorescence, of a dye that is incorporated into the sample material and that varies in a detectable manner as the number of copies of the original DNA molecule increases and/or as the DNA transitions from double stranded DNA (dsDNA) to single stranded DNA (ssDNA) with increasing temperature. The accuracy and reliability of nucleic acid assays depends, to a large extent, on the accuracy and precision of such imaging systems. Moreover, the costs of such imaging systems are a significant portion of the cost of an overall instrument for performing nucleic acid assays.

Thus, there is a continuing need for improvements in accuracy, precision, and cost effectiveness of imaging systems for monitoring nucleic acid diagnostic assays and other biological processes.

SUMMARY

Using a 2 dimensional CMOS or CCD sensor to image a fluorescence source is known in biological studies. Usually a microscope lens is used to image the fluorescence source into scientific CMOS/CCD sensor. In accordance with aspects of the present invention, improved imaging and/or lower cost imaging systems are achieved by using a digital single lens reflex ("DSLR") camera as the imaging device in combination with LED excitation sources of a prescribed configuration and arrangement described herein. Such an imaging system has many advantages, including:

(1) The large CMOS sensor of the DSLR camera allows both flow tracking and thermal melt measurements using the same camera.

(2) The 8-bit JPEG format of the DSLR camera saves data transfer bandwidth and hard drive spaces compared with 14-bit RAW data. Bit depth can be restored by averaging many pixels.

(3) A sensor with large pixel density, such of the DSLR camera, permits reactions in the microfluidic channel to be observed. Information such as bubble formation could be obtained to have better control of the PCR and thermal melt process.

(4) Due to large CMOS sensor size of the DSLR camera, reference fluorescence materials could be used to correct for and remove fluctuations from the light source and the heater.

Thus, aspects of the invention are embodied in an imaging system configured to generate images of a reaction within a microchannel of a microfluidic device. In one embodiment, the imaging system comprises a sensor element configured to generate a storable image of at least a portion of a microchannel and a plurality of illumination elements disposed with respect to the sensor element and configured to illuminate a portion of the microfluidic chip to be imaged by the sensor element. At least one of the illumination elements comprises an illumination assembly comprising an LED, a mask disposed in front of the LED and having an opening formed therein so as to control an area illuminated by the illumination assembly, a filter along an optic path of the illumination assembly for controlling the spectral content of light emitted by the illumination assembly, and a lens for imaging an area with light emitted by the illumination assembly. The LED, the mask, the filter, and the lens are aligned along an optic axis of the illumination assembly.

In one embodiment, at least two of the illumination elements are configured to illuminate different portions of the microfluidic chip.

In another embodiment, the sensor element comprises a digital single lens reflex camera.

In another embodiment, each of the illumination elements comprises an LED.

In another embodiment, the imaging system comprises four illumination elements disposed at 90-degree angular increments about the sensor element.

In another embodiment, the microchannel comprises a first zone and a second zone, wherein a first one of the LEDs is positioned and oriented to illuminate the second zone, a second and a third of the LEDs are spaced 180-degrees from each other and are disposed on opposed sides of the sensor and are positioned and oriented to illuminate the first zone, and wherein a fourth one of the LEDs is positioned and oriented to illuminate both the first zone and the second zone.

In another embodiment, the sensor element comprises a CMOS sensor.

In another embodiment, the CMOS sensor has a pixel array of up to 5616×3744 pixels or higher.

In another embodiment, the sensor element includes a pixel array, and the system further comprises logic elements configured to detect an image of only a portion of the pixels of the pixel array.

In another embodiment, the sensor element is configured to generate multiple images at a frequency of up to 30 Hz or higher.

In another embodiment, the sensor element is configured to generate an image having an 8-bit JPEG format.

In another embodiment, the imaging system further comprises reference fluorescence material positioned to be imaged by the sensor element along with at least a portion of a microchannel.

In another embodiment, the imaging system further comprises at least one extension tube between the sensor and the microchannel. In other embodiments, lens combinations may be used in place of extension tubes.

In another embodiment, the imaging system further comprises an emission filter positioned between the sensor and the microchannel and is configured to allow light signals of only a selected wavelength to reach the sensor.

In another embodiment, each of the plurality of illumination elements is configured to illuminate a portion of the microfluidic chip at a prescribed wavelength.

Further aspects of the invention are embodied in a system for performing a nucleic acid diagnostic assay on a sample material. In one embodiment, the system comprises microfluidic means including micro-channels for transporting sample material and for enabling an assay process to be performed on sample material within one or more portions of the micro-channels. The assay process includes at least one of PCR amplification and/or thermal melt analysis. The system further includes means in operative cooperation with the microfluidic means for introducing sample material into the micro-channels of the microfluidic means; means in operative cooperation with the microfluidic means for moving sample material through each micro-channel of the microfluidic means, thermal means for heating and/or cooling one or more portions of the microfluidic means to one or more selected temperatures, and imaging means for imaging sample material within one or more portions of each micro-channel, including means for storing data related to images created by the imaging means.

In another embodiment, the system further comprises processing means for processing data related to images created by the imaging means and for generating data relating to results of at least one of the PCR amplification and the thermal melt analysis.

In another embodiment, the system further comprises control means for controlling operation of the means for introducing sample material, the means for moving sample material, the thermal means, the imaging means, and the processing means.

In another embodiment, the imaging means is configured for detecting fluorescent emissions of prescribed wavelengths from sample material within the micro-channels and comprises means for directing an excitation signal of a prescribed excitation wavelength at a portion of the micro-channel and means for capturing an image of fluorescent emission of a prescribed emission wavelength from the sample material within the portion of the micro-channel.

Further aspects of the invention are embodied in a computer-implemented method for analyzing thermal melt data from an image of a reaction within a microchannel of a microfluidic device. In one embodiment, the method comprises the steps of illuminating at least a portion of the microchannel, generating, with a pixel array sensor, an image of fluorescence emitted by material within the illuminated portion of the microchannel, wherein each pixel of the image has a JPEG value, defining a region of interest ("ROI") comprising a portion of the pixels of the pixel array, and calculating the intensity of fluorescence emitted by material within the microchannel by averaging the JPEG values of all the pixels in the ROI.

In another embodiment, each pixel has two sub-pixels of a first color and one sub-pixel of a second color, and the JPEG value of each pixel is computed as (2×first color sub-pixel+ 1×second color sub-pixel)/3.

In another embodiment, the method further comprises dividing at least a portion of the ROI into one or more sub-ROIs and calculating fluorescence intensity within each sub-ROI by averaging JPEG values of all the pixels in the sub-ROI.

In another embodiment, the generating step is performed with a CMOS sensor.

In another embodiment, the CMOS sensor comprises a digital single lens reflex camera.

In another embodiment, the method further comprises repeating the generating and calculating steps one or more times over a period of time and monitoring changes in the calculated fluorescence intensity over a period of time.

In another embodiment, the method further comprises monitoring a fluid flow within the microchannel by generating images of fluorescence emitted by material within the illuminated portion of the microchannel at two different times, detecting displacement of a feature of the image within from one image to the next, and computing a time lapse from one image to the next.

In another embodiment, the method further comprises illuminating a reference fluorescence material positioned adjacent the microchannel, generating, with the pixel array sensor, an image of fluorescence emitted by the reference fluorescence material, and defining at least two ROIs, wherein one ROI encompasses the portion of the microchannel and a second ROI encompasses a portion of the reference fluorescence material.

In another embodiment, the method further comprises calculating the intensity of fluorescence emitted by the reference fluorescence material by averaging the JPEG values of all the pixels in the ROI encompassing the reference fluorescence material and adjusting the intensity of fluorescence emitted by material within the microchannel based on the intensity of fluorescence emitted by the reference fluorescence material.

Further aspects of the invention are embodied in a computer-implemented method for analyzing thermal melt data. In one embodiment, the method comprises recording thermal melt image data as a function of time with an imaging system by saving JPEG images generated by the imaging system with time stamps, recording temperature data as a function of time with a temperature control system, and synchronizing the thermal melt data with the temperature data by sending a static record signal to the imaging system to cause the imaging system to record static image data before thermal melt is started, recording the time of the static image data, and synchronizing the temperature data to the time of the static image data.

In another embodiment, the method comprises sending the static image signal to the imaging system at the same time an initial heater signal is sent to the temperature control system, so that the thermal melt image data and heaters controlled by the temperature control system will have the same start time, and then synchronizing the temperature data and the thermal melt image data based on a relationship of the time of the static image data to the time stamps of the JPEG images of the thermal melt image data and recorded time of the temperature data.

These and other features, aspects, and advantages of the present invention will become apparent to those skilled in the art after considering the following detailed description, appended claims and accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

Systems for nucleic acid analyses using microfluidic chips with one or more micro-channels, such as the system described in the aforementioned '230 publication, the '560 patent, and the real-time PCR architecture described in the aforementioned '124 patent, include an image sensor (or optical imaging system) for detecting optically-detectable characteristics of a sample flowing through a micro-channel, such as amplification products and flow rate of the test solution. Test solution flowing through each micro-channel may be in the form of discrete boluses of sample solution separated by carrier fluid, as described in the '124 patent.

Figure 1:
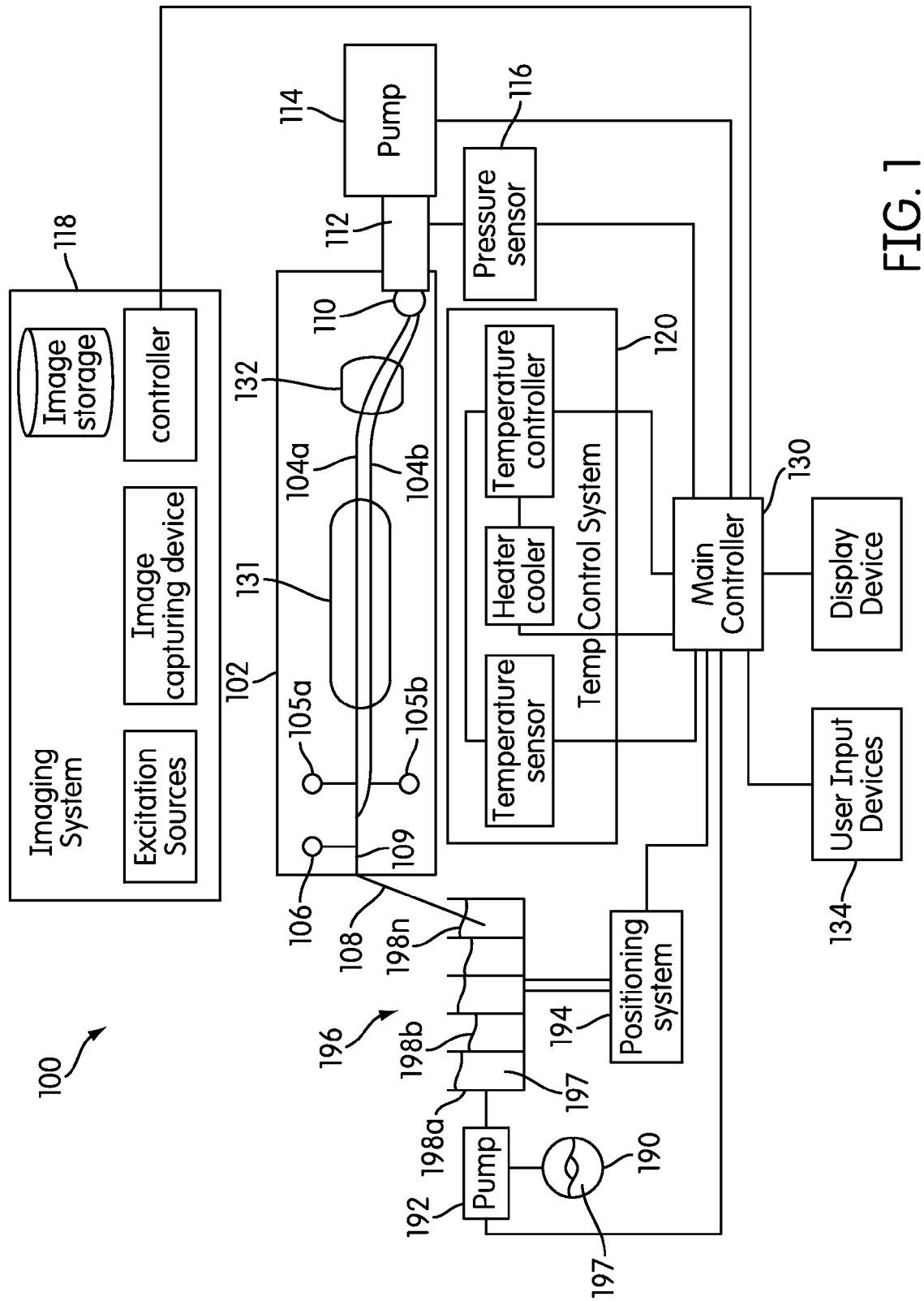
FIG. 1 is a block diagram illustrating a system in which an imaging system incorporating aspects of the invention can be incorporated.

FIG. 1 is a block diagram illustrating a system 100 for rapid serial processing of multiple nucleic acid assays that can be configured to embody various aspects of the invention. System 100 may include a microfluidic device 102. Microfluidic device 102 may include one or more microfluidic channels 104. In the examples shown, device 102 includes two microfluidic channels, channel 104a and channel 104b. Although only two channels are shown in the exemplary embodiment, it is contemplated that device 102 may have fewer than two or more than two channels. For example, in some embodiments, device 102 includes eight channels 104.

In one embodiment, device 102 may include two DNA processing zones, a DNA amplification zone 131 (a.k.a., PCR zone 131) and a DNA thermal melting zone 132. A DNA sample traveling through the PCR zone 131 may undergo PCR, and a DNA sample passing through thermal melting zone 132 may undergo high resolution thermal melting. As illustrated in FIG. 1, PCR zone 131 includes a first portion of channels 104 and thermal melting zone 132 includes a second portion of channels 104, which is down stream from the first portion.

Device 102 may also include a sipper 108. Sipper 108 may be in the form of a hollow tube. Sipper 108 has a proximal end that is connected to an inlet 109 which inlet couples the proximal end of sipper 108 to channels 104. As an alternative to, or in addition to, the sipper 108, the system may include a liquid handling system comprising at least one robotic pipettor for aspirating, mixing, and dispensing reagent and/or sample mixtures to the microfluidic cartridge 102.

Device 102 may also include a common reagent well 106 which is connected to inlet 109. Device 102 may also include a locus specific reagent well 105 for each channel 104. For example, in the embodiment shown, device 102 includes a locus specific reagent well 105a, which is connected to channel 104a, and may include a locus specific reagent well 105b which is connected to channel 104b. Device 102 may also include a waste well 110 for each channel 104.

The solution that is stored in the common reagent well 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the channels 104, system 100 may include a well plate 196 that includes a plurality of wells 198, at least some of which contain a sample solution (e.g., a solution containing a nucleic acid sample). In the embodiment shown, well plate 196 is connected to a positioning system 194 which is connected to a main controller 130.

In one non-limiting embodiment, main controller 130 may be implemented using a PXI-8105 controller which is available from National Instruments Corporation of Austin, Tex. In one non-limiting embodiment, positioning system 194 may include a positioner (e.g., the MX80 positioner available from Parker Hannifin Corporation of PA ("Parker")) for positioning well plate 196, a stepping drive (e.g., the E-AC Microstepping Drive available from Parker) for driving the positioner, and a controller (e.g., the 6K4 controller available from Parker) for controlling the stepping drive.

In one embodiment, to introduce a sample solution into the channels 104, the positioning system 194 is controlled to move well plate 196 such that the distal end of sipper 108 is submerged in the sample solution stored in one of the wells 198. FIG. 1 shows the distal end of 108 being submerged within the sample solution stored in well 198n.

In order to force the sample solution to move up the sipper and into the channels 104, a vacuum manifold 112 and pump 114 may be employed. The vacuum manifold 112 may be operably connected to a portion of device 102 and pump 114 may be operably connected to manifold 112. When pump 114 is activated, pump 114 creates a pressure differential (e.g., pump 114 may draw air out of a waste well 110), and this pressure differential causes the sample solution stored in well 198n to flow up sipper 108 and through inlet channel 109 into channels 104. Additionally, this causes the reagents in wells 106 and 105 to flow into a channel. Accordingly, pump 114 functions to force a sample solution and real-time PCR reagents to flow through channels 104. As illustrated in FIG. 1, melt zone 132 is located downstream from PCR zone 131. Thus, a sample solution will flow first through the PCR zone and then through the melting zone.

Referring back to well plate 196, well plate 196 may include a buffer solution well 198a. In one embodiment, buffer solution well 198a holds a buffer solution 197. Buffer solution 197 may comprise a conventional PCR buffer, such as a conventional real-time (RT) PCR buffer. Conventional PCR buffers are available from a number of suppliers, including, for example: Bio-Rad Laboratories, Inc., Applied Biosystems, Roche Diagnostics, and others.

In order to replenish buffer solution well 198a with the buffer solution 197, system 100 may include a buffer solution storage container 190 and a pump 192 for pumping the buffer solution 197 from container 190 into well 198a. Additionally, pump 192 may be configured to not only add solution 197 to well 198a, but also remove solution 197 from well 198a, thereby re-circulating the solution 197.

In one configuration, as described in the '124 patent, the system includes a test solution reservoir, which as described above, may be a reservoir containing multiple test solutions, such as a multi-well, microtiter plate 196 in which each well contains different test solutions, e.g., test samples. The system further includes a carrier fluid reservoir. In one embodiment, the test solution is substantially the same as the carrier fluid, except that the test solution comprises all the necessary real-time PCR reagents. The real-time PCR reagent mixture may include PCR primers, dNTPs, polymerase enzymes, salts, buffers, surface-passivating agents, and the like. In addition, the real-time PCR mixture may include a non-specific fluorescent DNA detecting molecule, a sequence-specific fluorescent DNA probe or a marker. In an additional embodiment, the carrier fluid is an immiscible fluid (such as an oil, a fluorinated liquid, or any other nonaqueous or hydrophobic solvent). The purpose of the carrier fluid is to deter transfer of material from one test bolus to another. Another purpose of the carrier fluid is to provide a distinguishable transition between boluses that may be used to track the fluid flow in the channel. In one embodiment, the carrier fluid may include a marker.

In one embodiment, the test solution and carrier fluid are introduced into a microchannels 104a, 104b through a switch (not shown) under control of the main controller 130 such that the carrier fluid and the test solution are sequentially alternately introduced into microchannels 104a, 104b to form discrete boluses of test solution separated from one another by carrier fluid. The volume of the test solution and carrier fluid that is introduced into microchannels 104a, 104b is selected such that there is minimal blending between them during movement through microchannels 104a, 104b.

A multitude of reactions in series (or sequential reactions) can thus be carried out in each of the microchannels 104a, 104b as a result of the continuous movement of boluses of different test solutions through microchannels 104a, 104b, each separated by the carrier fluid. The flow rate of the carrier fluid and test solution boluses through microchannels 104a, 104b is controlled by pump 114 under control of main controller 130 in order to regulate the flow rate of the test solution boluses and the carrier fluid in microchannels 104a, 104b. The flow rate may be regulated such that a desired number of PCR cycles are performed as the test solution boluses passes through PCR zone 131 of the microchannels 104a, 104b.

In order to achieve PCR for a DNA sample flowing through the PCR zone 131, the temperature of the sample must be cycled, as is well known in the art. Accordingly, in some embodiments, system 100 includes a temperature control system 120. The temperature control system 120 may include a temperature sensor, a heater/cooler, and a temperature controller. In some embodiments, a temperature control system 120 is interfaced with main controller 130 so that main controller 130 can control the temperature of the samples flowing through the PCR zone and the melting zone. Although a single temperature control system 120 is shown for the entire microchip 102, the temperature control system 120 may comprise separate temperature control sub-systems—each comprising, for example, a temperature sensor, a heater/cooler, and a temperature controller—for the PCR zone 131 and the melt zone 132.

Main controller 130 may be connected to a display device for displaying a graphical user interface. Main controller 130 may also be connected to user input devices 134, which allow a user to input data and commands into main controller 130.

To monitor the PCR process and the melting process that occur in PCR zone 131 and melt zone 132, respectively, system 100 may include an imaging system 118. Imaging system 118 may include an excitation source, an image capturing device, a controller, and an image storage unit. According to an embodiment of the invention, the imaging system 118 comprises a CMOS sensor that, in one embodiment, may comprise part of an off-the-shelf digital single-lens reflex (DSLR) camera, which has a large format CMOS sensor (such as, for example, 24 mm×36 mm). The field of view is much larger than prior systems that employ microscope lenses and allows imaging of the entire microfluidic chip. The imaging system 118 could be used for both flow tracking of the microfluidic system and thermal melt signal detection.

Methods for flow tracking, i.e., measuring flow rate through the micro channels 104a, 104b, are described in the '124 patent. For example, in one embodiment, the average flow rate is measured by comparing sequential images of the reaction-dependent fluorescent signal from the channel. In a second embodiment, the average flow rate is measured by comparing sequential images of a reaction-independent flow marker from the channel. More specifically, the system acquires one or more images of the contents of the channel. These image data and the time of acquisition are stored to a database for subsequent analysis. A feature of two or more sequential images—e.g., reaction-dependent fluorescent signal from the channel or reaction-independent flow marker from the channel—may be compared to determine how far the fluid has moved along the channel from one image to a subsequent image. Dividing the average displacement by the elapsed time gives an average flow speed. In another embodiment, scattered light from the reaction-independent flow marker is resolvable from the reaction-dependent fluorescence by wavelength spectrum. In an alternative embodiment, scattered light from the reaction-independent flow marker is resolvable from the reaction-dependent fluorescence on the basis of fluorescence lifetime. In another embodiment, the reaction-independent flow marker is further used to determine the flow dispersion of the test bolus. In a further embodiment, the image of reaction-dependent fluorescence is captured at least once per PCR cycle. In one embodiment, the image of reaction-dependent fluorescence is captured sequentially by scanning a length of the channel on a time scale shorter than the duration of one PCR cycle. In an alternative embodiment, the image of reaction-dependent fluorescence is captured by acquiring signals from multiple points along the channel simultaneously. In another embodiment, the flow rate measurements are part of a feedback loop for regulating the flow rate. In a further embodiment, the flow rate is measured through detecting a sample bolus entrance into and exit from a defined section of the channel.

In some embodiments, the determined flow rate may be used as an input to control the pump 114, via the main controller 130, in a feedback flow control loop.

More specifically, in an embodiment of the invention, a digital single-lens reflex (DSLR) camera is employed for high resolution thermal melt and flow tracking in microfluidic chips. In a non-limiting example, the DSLR camera can be a Canon EOS 5D Mark II. The DSLR camera is also suitable to acquire real-time PCR information (as described, for example, in the '124 patent) when applicable. Usually, digital cameras save pictures in RAW or JPEG format. To achieve a fast frame rate, JPEG format is usually adopted. In one non-limiting embodiment, the DSLR camera has a CMOS sensor of 24 mm×36 mm, with a pixel array of 5616×3744, or higher, arranged in a Bayer pattern (2 Green, 1 Blue, 1 Red sub-pixel for each pixel).

To record fluorescence change over time during DNA thermal melt, a high frame rate is preferred. In one embodiment, the detector can be a digital color camera that is capable of recording data at video frames rates, such as, for example, 20-30 frames per second. The live view function of a suitable DSLR camera, such as, for example, the Canon EOS 5D Mark II, provides a frame rate of 30 fps. Of course, a suitable DSLR camera with a higher or lower frame rate may be used as well in certain embodiments. In a non-limiting example, files from the live view function are saved in JPEG format with two choices of resolutions:

a. full sensor images with sub-sampled pixels, image size 1024×680 (1× zoom); and b. a crop of the sensor with full pixel resolution, image size 1120×752 (5× zoom).

In one embodiment, the 1× zoom is used for flow tracking, since it images a relatively large area (at a reduced pixel density), which may include portions of the microfluidic chip where PCR and thermal melt occur and part of an interface chip coupled to the microfluidic chip for liquid handling. In one embodiment, the 5× zoom is used for thermal melt detection where increased resolution (detail) of a small portion of the microfluidic chip is required. In a preferred embodiment, all the pixels in the imaged area are preserved so better signal to noise ratio (SNR) can be achieved. In other embodiments, a different zoom setting could be used for either flow tracking or thermal melt detection.

JPEG image format offers 8-bit resolution, i.e., 256 digital levels for each pixel. In some embodiments, more bit depth could be achieved by averaging many pixels in the region of interest ("ROI") to achieve greater than 8-bit resolution.

As described in the '560 patent, the pixel array of the sensor may be divided into zones of interest corresponding to particular ROI's. That is, the image sensor has the ability to read out or "window" a predefined portion of the pixel array (this is known as "windowing"). For thermal melt imaging, the melting zone 132 of the micro-channel 104a, 104b is uniformly illuminated with a high power LED and is imaged into the CMOS sensor with ~1:1 ratio. In the melting zone 132 where thermal melt is measured, the fluorescence intensity is calculated by averaging the JPEG values of all the pixels in the ROI. In one embodiment, fluorescence intensity is calculated by averaging JPEG values of >2000 pixels. By averaging pixel JPEG values (8-bit) of an ROI with numerous pixels, better than 11 bit resolution could be achieved.

Another benefit from averaging the pixels in the ROI is to improve signal-to-noise ratio ("SNR").

Fluorescence from LC Green (DNA binding dye used for high resolution melting) is nearly equally sensed by green and blue pixels of the CMOS sensor. Thus, the average of the green and blue pixels is used to represent the fluorescence intensity on that specific pixel of the sensor. Because of the Bayer filter in front of the sensor in accordance with one embodiment, in each pixel there are 2 green pixels and 1 blue pixel. Accordingly:

$$\text{Pixel fluorescence intensity} = (2*\text{Green} + 1*\text{Blue})/3.$$

In reality, the weight of Green and Blue may deviate from the 2:1 ratio due to other camera settings. One such setting that can affect the Green to Blue ratio is white balance. White balance manipulates green, blue, and red pixel JPEG values to adapt the image to different illumination conditions. Using SNR as a metric, optimized condition of white balance settings and green, blue ratio could be calculated or measured.

Figure 2:
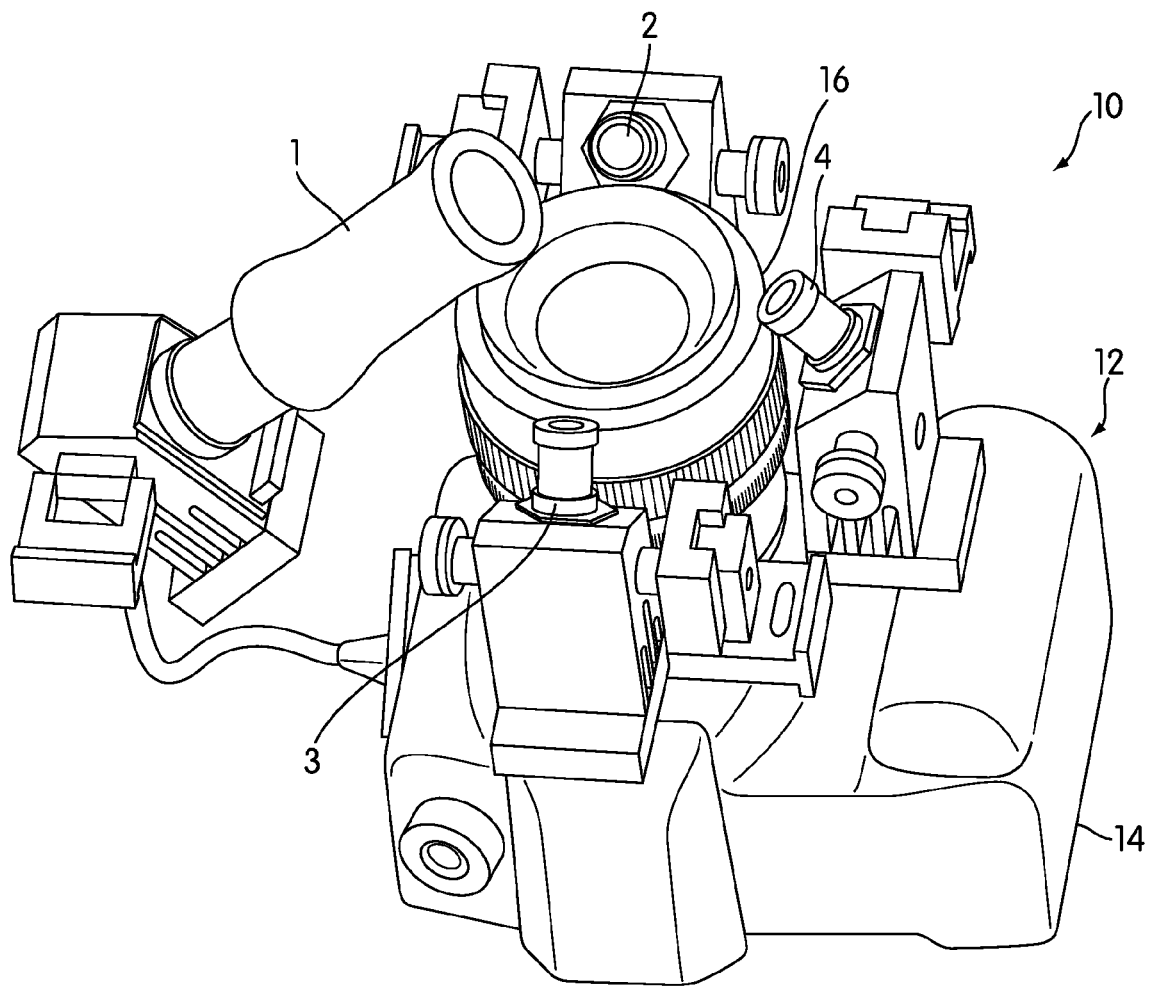
FIG. 2 is a perspective view of an imaging system including a sensor and LED layout according to an embodiment of the invention.
Figure 3:
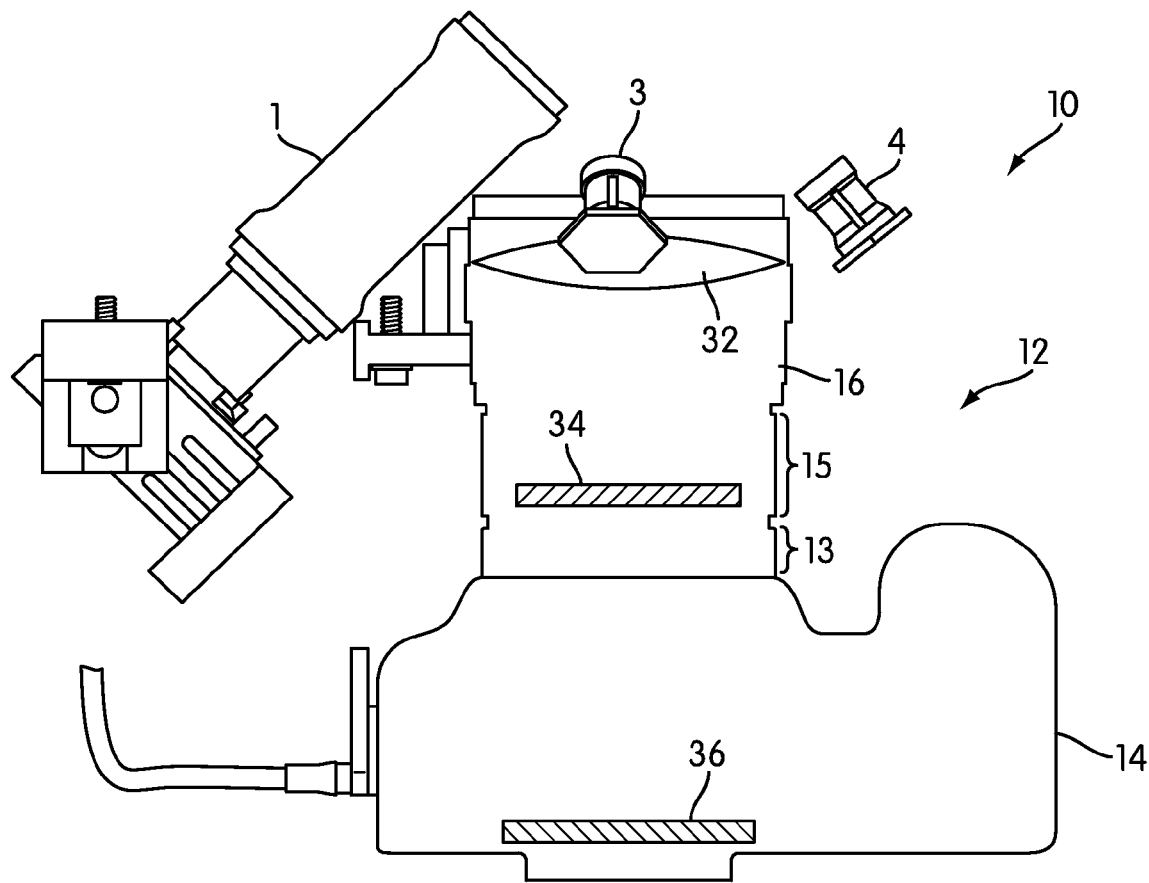
FIG. 3 is a side view of an imaging system including a sensor and LED layout according to an embodiment of the invention.

An imaging system 10, according to an embodiment of the invention, is shown in FIGS. 2 and 3. The imaging system 10 includes a CMOS sensor 36, which, in one embodiment, is housed within the body 14 of a camera 12, for example, a DSLR camera, such as the Canon EOS 5D Mark II, and a lens barrel 16 containing one or more lenses 32. In embodiments of the invention, the imaging system 10 may be used for thermal melt measurement and flow tracking. In one embodiment, the imaging system 10 is configured to generate and record multiple images per second for flow tracking and thermal melt analysis. For example, the Canon EOS 5D Mark II includes a live view mode that is used to generate and record JPEG images at ~1 Hz for flow tracking purposes while boluses flow in microfluidic channels. It could also be used for real-time PCR purposes. In certain embodiments, for thermal melt data recording, images, such as JPEG files, are recorded at ~30 Hz rate, with integration time ~33 ms (i.e., the integration time interval is computed as 1/freq.). Other frame rates and corresponding integration time intervals may be employed, depending on system requirements and hardware capability, but frame rates are preferably not less than 10 Hz.

In one embodiment, an F/1.2 lens, which is commercially available, may be used for greater photon collection. Lenses with smaller F/# have higher light collection capability.

Extension tubes 15, 13 may be used to make the distance between lens 16 and the microfluidic chip to be imaged as close as possible. Light collection is proportional to the square of distance between lens and fluorescence source. In one embodiment, the extension tubes have lengths of 25 mm and 12 mm, for a total extension length of 37 mm, which can make the distance between lens 16 and the microfluidic chip to be imaged as close as about 6 cm. Other extension tube lengths could be used, such as, for example, 25 mm and 25 mm. In addition, more or less than two extension tubes can be employed. For example, other embodiments may include three extension tubes of 25 mm, 25 mm, and 12 mm or 25 mm, 25 mm, and 25 mm. Longer extension tubes make the distance between lens and the microfluidic chip smaller, which allows more light to enter the lens and which could also could make the image on the sensor larger. The choice of extension tubes may depend on specific mechanical design and field of view considerations. As an alternative to the use of extension tubes, lens combinations could be used to achieve the same goal of moving the lens closer to the sample material in the microfluidic chip and providing larger images.

The sensor may include a dual band emission filter 34, which may be fitted in one of the extension tubes 15, 13 to allow only selected wavelengths to reach the sensor. In one embodiment, the filter is configured to allow only fluorescence from LC Green and Alexa 647 (or Texas Red) tracking dye to reach the sensor. In one exemplary embodiment, the emission filter is a dual bandpass filter with a pass-band for the DNA binding dye LC Green Plus from Idaho Technology and a pass-band for a red flow tracking dye such as AlexaFluor 647 from Life Technologies. However, alternative filters may be substituted for appropriate alternative combinations of fluorescent dyes. Fluorescence from LC Green has a blue-green color that is sensed by both blue and green pixels of the CMOS sensor. However, because the camera's green filter will block blue photons, and the camera's blue filter will block green photons, at least half of the photons are rejected by either filter. In one embodiment, the filter has a shifted spectrum (e.g., to the blue-green wavelength) so all the photons could pass the filter to reach the sensor pixels. The camera's red filter can be kept unchanged so the 'dual color' sensor can still do both flow tracking and thermal melt detection with two different dyes.

In one embodiment, the imaging system 10 includes four LEDs 1, 2, 3, 4 for illumination of the microfluidic chip. The LEDs are excitation sources that generate light at desired wavelengths to excite labels used for detecting amplification products during real-time PCR, dissociation behavior during thermal melt analysis, and/or to detect markers that may be present to monitor the flow rate of the test solution in microchannel 104a and/or 104b. As explained above, PCR zone 131 of the chip is for PCR, and melting zone 132 is for thermal melt. An embodiment of the layout of the sensor 12 and LEDs 1, 2, 3, 4, of the imaging device 10 is shown in FIGS. 2 and 3. FIG. 2 is an illustration of an imaging device 10, including the sensor (e.g., camera) 12 and the LED layout. As shown in the illustrated embodiment, the LEDs 1, 2, 3, 4 are arranged adjacent to the lens(es) 16 (lens barrel) at 90° angular intervals around the lens 16. LEDs 2 and 3 are disposed opposite each other with respect to the lens 16, and LEDs 1 and 4 are disposed opposite each other with respect to the lens 16.

In an exemplary embodiment, LED 1 comprises an assembly with a slot aperture and an imaging lens and is positioned and oriented for melting zone 132 (thermal melt) illumination. LED 2 and LED 3 are positioned and oriented for PCR zone 131 (PCR) heater calibration and can also be used to monitor PCR process and melt in zone 131 if necessary. LED 4 is positioned and oriented to excite flow tracking dye in the whole chip 102. In one embodiment, a goal is to limit illumination of LED 4 to PCR zone 132, thus avoid photobleaching in melting zone 131 when doing thermal melt.

Figure 4:
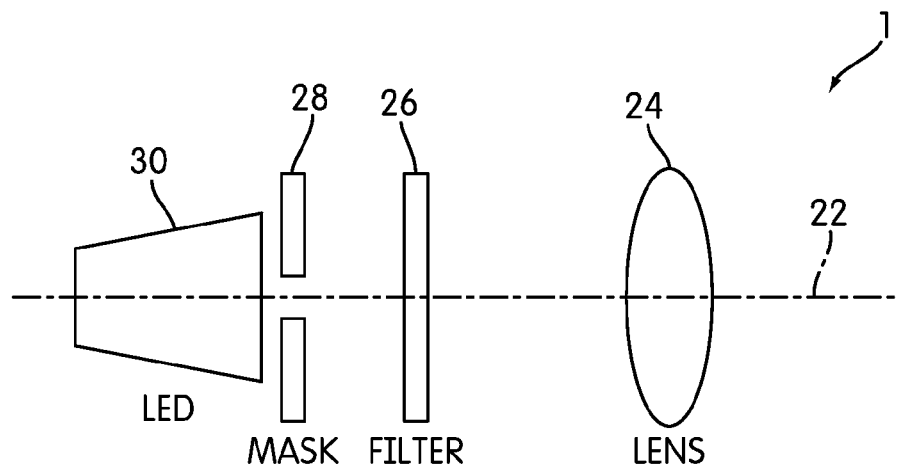
FIG. 4 is a schematic view of an LED assembly of the imaging system according to an embodiment of the invention.

FIG. 4 is a schematic view of the melting zone 132 LED (LED 1) assembly in accordance with one embodiment. As shown in FIG. 4, LED 1 is actually an assembly that includes an LED 30, a mask 28, a filter 26, and a lens 24 aligned along an optic axis 22. Mask 28 includes a slot for limiting the illumination from the LED 30 to thermal melt zone 132 of the microfluidic chip 102. Filter 26 controls the spectral content of excitation light directed at the chip 102, and lens 24 images the light band onto melting zone 132. Melting zone 132 is illuminated with the band shape light from the mask 28 of the LED assembly 1. With the band-shaped light, this LED (blue LED) illuminates only melting zone 132, so as to avoid photobleaching of the dye in PCR zone 131. The assembly may also include heat sinks and fans.

In one embodiment, two high-powered blue LEDs (2, 3) are placed at both sides of PCR zone 131 to excite LC Green in zone 131 for heater calibration. In an embodiment of a system for nucleic acid analyses using a microfluidic chip with one or more micro-channels, the heating element may comprise metal wires or filaments disposed adjacent to the micro-channels, for example, as disclosed in U.S. Patent Application Publication No. 2009-0248349 "Microfluidic Devices with Integrated Resistive Heater Electrodes Including Systems and Methods for Controlling and Measuring the Temperature of Such Heater Electrodes" and U.S. Patent Application Publication No. 2011-0048547 "Microfluidic systems and methods for thermal control," the disclosures of which are hereby incorporated by reference in their entireties.

In one embodiment, LEDs 2 and 3 are disposed on opposite sides of the microfluidic chip 102 to avoid shadow in PCR zone 131 due to the heater elements. Additionally, this disposition of LEDs 2 and 3 creates more uniform illumination across all channels. Heater calibration can be performed by passing a substance with a known nucleic acid concentration through a micro-channel 104a, 104b, illuminating melting zone 132 with LED 1 and generating thermal melt curves that are compared to expected thermal melt curves for the known nucleic acid concentration. In some embodiments, LEDs 2 and 3 could also be used to monitor PCR and thermal melt in zone 131.

In one embodiment, LED 4 (red LED) flood illuminates the whole chip 102, which can be used for flow tracking purposes In preferred embodiments, all of the LEDs 1, 2, 3, 4 and the sensor 12 are facing up, and the transparent side of the microfluidic chip 102 faces down. This arrangement allows a liquid handling system (e.g., robotic pipetter) to use the space above the chip 102 with minimal obstacles.

In preferred embodiments, LEDs 1, 2, 3, 4 are controlled by a controller of the imaging system 118 and/or the main controller 130 executing control algorithms written, in one non-limiting example, in Labview from National Instruments. Other control algorithms also can be used as would be known by persons skilled in the art.

It is understood that the CMOS sensor of imaging system 10 need not be a DSLR camera. In embodiments of the present invention, the CMOS sensor of imaging system 10 can be another suitable sensor having the characteristics described herein.

In certain embodiments, when heaters are not uniform, only a small portion of melting zone 132 may be used as the ROI (the thermally uniform portion). Typically, the uniform portion of melting zone 132 corresponds to that part of melting zone 132 heated by calibrated heating elements, and the non-uniform, fringe portions of melting zone 132 include non-calibrated heating elements. An effectively larger ROI can be created under conditions of non-uniform heating by dividing the non-uniform ROI portion of melting zone 132 into several smaller "sub-ROIs", each of which is small enough to have a uniform temperature. In some embodiments, melt curves are plotted for each small sub-ROI and are then shifted to the temperature calibrated region in the ROI mathematically to correlate the melt curves of the non-calibrated sub-ROIs with the melt curve of the ROI of the calibrated portion of melting zone 132. SNR could be improved with the larger effective ROI. Alternatively, in an embodiment where the heater is calibrated, a ROI over the uniformly heated section of the heater is used, so the temperature of this specific ROI is calibrated and can be assumed to be accurate. The edges of the heater usually have a different temperature than the calibrated ROI. The temperature difference between the regions on the heater edges and the calibrated ROI can be calculated. For example, when material in the calibrated ROI melts at 70° C. and the material at the edges melts at 80° C. (reading of the heater temperature calibrated using the ROI), it is known that the edge is 10° C. cooler than the calibrated ROI. Edges of the heater will melt later but the temperature axis can be adjusted using the temperature difference data. Thus, the heater edges could have the same temperature axis as the calibrated ROI. The melt curves of more ROIs along the heater can be shifted to the calibrated ROI and added up to generate a melt curve with better SNR.

Reference fluorescence materials could be placed near the sample (without interfering with the fluorescence from the sample) so that fluctuations from the light source can be identified and removed. That is, fluctuations from the expected fluorescence signal of the reference fluorescence materials can be identified so that corrections in the fluorescence signal measured from the sample material can be made. In addition, the reference fluorescence materials could be used to identify whether distortion is from the light source or a heater when debugging the system. That is, distortions that exhibit in both the reference fluorescence materials and the sample materials are likely due to excitation light source distortions, whereas distortions that exhibit in the sample materials but not in reference fluorescence materials are likely due to distortions in the heater. Such reference materials could be any fluorescence material that can be excited and detected by the imaging system 10. Suitable, non-limiting examples include Sytox blue, CFP, Alexa 647, Cy5, BODIPY650/665, or various quantum dots. In addition, the plastics in the microfluidic fixture could be used as fluorescence reference too.

In one embodiment, glue (e.g., Lens Bond Type SK-9 available from Summers Optical of Hatfield, Pa.) used to bond the microfluidic-chip and a heat sink can be used as reference.

The reference fluorescence material can be chosen to be temperature dependent. Heater fluctuation can be identified and removed using such reference fluorescence material. For example, when proper materials are chosen which have temperature dependent fluorescence intensity (fluorescence intensity of most dyes is temperature dependent, such as Alexa Fluor 647, fluorescein, et al), the temperature fluctuation of the heaters can be monitored using the fluorescence of the reference dye. When heater temperature changes, the fluorescence intensity of the reference dyes will follow the temperature changes. When the reference material has sufficient intensity and area, the fluorescence signal from the reference material measurement will have a sufficient SNR, so the change in fluorescence intensity could reflect the heater temperature fluctuations. In certain embodiments, the reference material may be placed close enough to the heaters for this purpose. The temperature dependence does not need to be same as the sample under measurement.

In some embodiments, only one detector is needed to measure both the sample fluorescence and reference fluorescence.

In one embodiment, thermal melt data is recorded by the imaging system 118 as a function of time (JPEGs are saved with their time stamps as file name). Temperature is also recorded by the temperature control system 120 as a function of time. This creates two data sets: an image vs. time data set and a temperature vs. time data set. Preferably, these two sets of data are synchronized accurately to give the correct melt temperature.

There are many ways to synchronize two independent data sets. In one embodiment, with a DSLR, a signal can be sent from a PC to the remote shooting control port of the camera to take a static image right before thermal melt is started. For example, the static image signal can be sent at the same time the initial heater signal is sent. Thus, both the images and the heaters will have the same start time. The time the static image is taken has a known relation with both the PC time (temperature time) and camera live view image time stamps, so the temperature and images can be synchronized, in some cases to within <30 ms resolution.

When imaging a uniform object, the images usually are not ideally uniform. The center will have higher intensity then the edges. In order to make melt data better, the microfluidic chip can be shifted so that melting zone 132 (where thermal melt occurs) is as close to the center of image as possible.

Aspects of the invention are implemented via control and computing hardware components, user-created software, data input components, and data output components. Hardware components include computing and control modules, such as main controller 130, such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed, for example, on display device 132, or otherwise indicated to a user for providing information to the user, for example, information as to the status of the instrument or a process being performed thereby, or such outputs may comprise inputs to other processes and/or control algorithms. Data input components comprise elements by which data is input for use by the control and computing hardware components. Such data inputs may comprise positions sensors and motor encoders, as well as manual input elements via user input devices 134, such as key boards, touch screens, microphones, switches, manually-operated scanners, etc. Data output components may comprise hard drives or other storage media, monitors, printers, indicator lights, or audible signal elements (e.g., buzzer, horn, bell, etc). Software comprises instructions stored on non-transitory computer-readable media which, when executed by the control and computing hardware, cause the control and computing hardware to perform one or more automated or semi-automated processes.

Embodiments of the present invention have been fully described above with reference to the drawing figures. While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations are not intended to convey that the inventions require features or combinations of features other than those expressly recited in the claims. Accordingly, the present invention is deemed to include all modifications and variations encompassed within the spirit and scope of the following appended claims.

The invention claimed is:

1. A computer-implemented method for analyzing thermal melt data from an image of a reaction within a microchannel of a microfluidic device, comprising:
    illuminating at least a portion of the microchannel, wherein the microchannel is in thermal communication with a heat source;
    generating, with a pixel array sensor, an image of fluorescence emitted by material within the illuminated portion of the microchannel, wherein each pixel of the image has a JPEG value;
    defining a region of interest ("ROI") comprising a portion of the pixels of the pixel array and subdividing the ROI into two or more sub-ROIs, each sub-ROI corresponding to a uniformly heated portion of the microchannel; and
    calculating the intensity of fluorescence emitted by material within the microchannel by averaging the JPEG values of all the pixels in each sub-ROI corresponding to a uniformly heated portion of the microchannel.

2. The method of claim 1, wherein each pixel has two sub-pixels of a first color and one sub-pixel of a second color, and the JPEG value of each pixel is computed as (2×first color sub-pixel+1×second color sub-pixel)/3.

3. The method of claim 1, further comprising dividing at least a portion of the ROI into one or more sub-ROIs and calculating fluorescence intensity within each sub-ROI by averaging JPEG values of all the pixels in the sub-ROI.

4. The method of claim 1, wherein the generating step is performed with a CMOS sensor.

5. The method of claim 4, wherein the CMOS sensor comprises a digital single lens reflex camera.

6. The method of claim 1, further comprising repeating the generating and calculating steps one or more times over a period of time and monitoring changes in the calculated fluorescence intensity over a period of time.

7. The method of claim 1, comprising monitoring a fluid flow within the microchannel by:
    generating images of fluorescence emitted by material within the illuminated portion of the microchannel at two different times;
    detecting displacement of a feature of the image within from one image to the next; and
    computing a time lapse from one image to the next.

8. The method of claim 1, further comprising:
    illuminating a reference temperature dependent fluorescence material positioned adjacent the microchannel;
    generating, with the pixel array sensor, an image of fluorescence emitted by the reference fluorescence material; and
    defining at least two ROIs, wherein one ROI encompasses the portion of the microchannel and a second ROI encompasses a portion of the reference temperature dependent fluorescence material.

9. The method of claim 8, further comprising:
    calculating the intensity of fluorescence emitted by the reference temperature dependent fluorescence material by averaging the JPEG values of all the pixels in the ROI encompassing the reference temperature dependent fluorescence material; and
    adjusting the intensity of fluorescence emitted by material within the microchannel in response to temperature fluctuations of the heater based on the intensity of fluorescence emitted by the reference temperature dependent fluorescence material.

* * * * *